United States Patent [19]
Carol et al.

[11] Patent Number: 6,038,283
[45] Date of Patent: Mar. 14, 2000

[54] PLANNING METHOD AND APPARATUS FOR RADIATION DOSIMETRY

[75] Inventors: Mark P. Carol, Sewickley; Robert C. Campbell, Cranberry Twp.; Bruce Curran, Sewickley; Richard W. Huber, Harmony; Richard V. Nash, Allison Park, all of Pa.

[73] Assignee: Nomos Corporation, Sewickley, Pa.

[21] Appl. No.: 08/957,206

[22] Filed: Oct. 24, 1997

Related U.S. Application Data

[60] Provisional application No. 60/029,480, Oct. 24, 1996.

[51] Int. Cl.$^7$ .................................. A61B 5/01; A61B 5/10
[52] U.S. Cl. .............................................................. 378/65
[58] Field of Search ................................................ 378/65

[56] References Cited

U.S. PATENT DOCUMENTS

| | | | |
|---|---|---|---|
| 5,027,818 | 7/1991 | Bova et al. | 600/427 |
| 5,317,616 | 5/1994 | Swerdloff et al. | 378/65 |
| 5,351,280 | 9/1994 | Swerdloff et al. | 378/65 |
| 5,379,333 | 1/1995 | Toth | 378/16 |
| 5,394,452 | 2/1995 | Swerdloff et al. | 378/65 |
| 5,400,378 | 3/1995 | Toth | 378/16 |
| 5,511,549 | 4/1996 | Legg et al. | 600/436 |
| 5,513,238 | 4/1996 | Leber et al. | 378/65 |
| 5,602,892 | 2/1997 | Llacer | 378/65 |
| 5,647,663 | 7/1997 | Holmes | 600/407 |

FOREIGN PATENT DOCUMENTS

| | | |
|---|---|---|
| 0 560 331 A1 | 10/1993 | European Pat. Off. . |
| 0 695 560 A2 | 7/1996 | European Pat. Off. . |
| WO 90/14129 | 11/1990 | WIPO . |

OTHER PUBLICATIONS

"Wedge–Shaped Dose Distributions by Computer–Controlled Collimator Motion"; Kijewski et al; Med. Phys., vol. 5, Sep./Oct. 1978; pp. 426–429.

"Dosage Calculations in Radiation Therapy"; Urban & Schwarzenberg, 1979; W. L. Saylor and T. Ames; pp. 19–34.

"Treatment Plan Optimization for Conformal Therapy"; I. Rosen and R. Lane; pp. 357–360; The Use of Computers in Radiation Therapy, 1987.

"Shaping of Arbitrary Dose Distributions by Dynamic Multileaf Collimation"; P. Kallman et al.; Phys. Med. Biol., 1988, vol. 33, No. 11, pp. 1291–1300.

"Computer–Assisted Conformation Radiotherapy With a Variable Thickness Multi–Leaf Filter"; Kobayashi et al.; I. J. Radiation Oncology Biology Physics., Jun. 1989, vol. 16, pp. 1631–1635.

"Optimisation of Conformal Radiotherapy Dose Distributions by Simulated Annealing"; S. Web; Phys. Med. Biol. 1989, vol. 34, No. 10, pp. 1349–1370.

"Radiation Physics"; F. Bova; Stereotacit Neurosurgery; Neurosurgery Clinics of North America, vol. 1, No. 4, Oct. 1990, pp. 909–931.

"Optimization of Conformal Radiotherapy Dose Distributions by Simulated Annealing: 2. Inclusion of Scatter in the 2D Technique"; S. Webb; Phys. Med. Biol. 1991, vol. 36, No. 9, pp. 1227–1237.

"Optimization by Simulated Annealing of Three–Dimensional Conformal Treatment Planning for Radiation Fields Defined by a Multileaf Collimator"; S. Webb; Phys. Med. Biol. 1991, vol. 36, No. 9, pp. 1201–1226.

(List continued on next page.)

*Primary Examiner*—David Vernon Bruce
*Attorney, Agent, or Firm*—Tobor, Goldstein & Healey L.L.P.

[57] ABSTRACT

A method and apparatus for determining an optimized radiation beam arrangement for applying radiation to a tumor target volume while minimizing radiation of a structure volume in a patient, which uses an iterative cost function based on a comparison of desired partial volume data, which may be represented by cumulative dose volume histograms and proposed partial volume data, which may be represented by cumulative dose volume histograms for target tumors and tissue structures for delivery of the optimized radiation beam arrangement to the patient by a conformal radiation therapy apparatus.

47 Claims, 6 Drawing Sheets

OTHER PUBLICATIONS

"Algorithm for Dosimetry of Miltiarc Linear–Accelerator Stereotactic Radiosurgery"; Luxton et al.; Medical Physics, vol. 18, No. 6, Nov./Dec. 1991, pp. 1211–1222.

"The Generation of Intensity–Modulated Fields for Conformal Radiotherapy by Dynamic Collimation"; D. Convery and M. E. Rosenbloom; Phys. Med. Biol., 1992, vol. 37, No. 6, pp. 1359–1374.

"Intensity Modulated Radiation Therapy May Improve Tumor Control & Decrease Complications," Advance for Adminstrators in Radiology, Radiology Technology Profile, Jul. 1996.

Study number: 1008  Patient name: Sinus/Compare

Next Logical Step
Review the prescription, planning parameters and maximum dose to non-target structures.

If all are correct, approve the prescription.

Treatment Machine: Nomos Library 6MV
Immobilization: Talon on NomoGrip
Localization: No Localizer

Planning Goals

Number of fractions [39] over [50] days (inclusive)
☐ Deliver all table angles in each fraction

Load Planning Set

| Target Name | Bd | Goal (Gy) | Vol Below Goal (%) Bv | Min (Gy) A | Max (Gy) C |
|---|---|---|---|---|---|
| Target 1 | ▨ | 75.0 | 5 | 70.0 | 80.0 |
| Target 2 | ☐ | | | | |
| Target 3 | ▨ | | | | |

| Sensitive Structure Name | | Limit (Gy) Bd' | Vol Above Limit (%) Bv' | Min (Gy) A' | Max (Gy) C' | BU | BP |
|---|---|---|---|---|---|---|---|
| Tissue | ☐ | 70.0 | 20 | 0.0 | 80.0 | ☑ | ☐ |
| Brain Stem | ▨ | Bd' 55.0 | Bv' 10 | A' 50.0 | C' 60.0 | ☐ | ☑ |
| Spinal Cord | ▨ | Bd' 50.0 | Bv' 20 | A' 45.0 | C' 60.0 | ☐ | ☑ |
| Larynx | ▨ | | | | | ☐ | ☐ |
| Auditory Apparatus | ▨ | Bd' 10.0 | Bv' 10 | A' 50.0 | C' 15.0 | ☑ | ☐ |
| Esophagus | ▨ | | | | | ☐ | ☐ |
| Trachea | ▨ | | | | | ☐ | ☐ |
| Parotid Gland | ▨ | 35.0 | Bv' 50 | A' 30.0 | C' 70.0 | ☑ | ☐ |
| Thyroid Gland | ☐ | Bd' 55.0 | Bv' 10 | A' 45.0 | C' 60.0 | ☐ | ☑ |
| Ref 1 | ▨ | Bd' 70.0 | Bv' 90 | A' 55.0 | C' 80.0 | ☑ | ☐ |
| Brain | ▨ | | | | | ☐ | ☐ |
| Lymph Node(s) | ▨ | | | | | ☐ | ☐ |
| Orbits | ▨ | Bd' 55.0 | Bv' 10 | A' 45.0 | C' 65.0 | ☑ | ☐ |
| Tissue-equivalent | ▨ | | | | | ☐ | ☐ |
| External Avoidance | ▨ | | | | | ☐ | ☐ |

Approval Options

[Revert to Saved]  [Save without Approving]

[Approve Prescription and Compute Plan]

PLANNING METHOD AND APPARATUS FOR RADIATION DOSIMETRY

RELATED APPLICATION

This application claims the benefit of U.S. Provisional Application No. 60/029,488, filed Oct. 24, 1996.

BACKGROUND OF THE INVENTION

1. Field of the Invention

The invention relates to a method and apparatus for conformal radiation therapy of tumors with a radiation beam having a pre-determined, constant beam intensity.

2. Description of the Prior Art

Modern day radiation therapy of tumors has two goals: eradication of the tumor and avoidance of damage to healthy tissue and organs present near the tumor. It is known that a vast majority of tumors can be eradicated completely if a sufficient radiation dose is delivered to the tumor volume; however, complications may result from use of the necessary effective radiation dose, due to damage to healthy tissue which surrounds the tumor, or to other healthy body organs located close to the tumor. The goal of conformal radiation therapy is to confine the delivered radiation dose to only the tumor volume defined by the outer surfaces of the tumor, while minimizing the dose of radiation to surrounding healthy tissue or adjacent healthy organs.

Conformal radiation therapy has been traditionally approached through a range of techniques, and typically uses a linear accelerator ("LINAC") as the source of the radiation beam used to treat the tumor. The linear accelerator typically has a radiation beam source which is rotated about the patient and directs the radiation beam toward the tumor to be treated. The beam intensity of the radiation beam is a predetermined, constant beam intensity. Multileaf collimators, which have multiple leaf, or finger, projections which can be moved individually into and out of the path of the radiation beam, can be programmed to follow the spatial contour of the tumor as seen by the radiation beam as it passes through the tumor, or the "beam's eye view" of the tumor during the rotation of the radiation beam source, which is mounted on a rotatable gantry of the linear accelerator. The multiple leaves of the multileaf collimator form an outline of the tumor shape as presented by the tumor volume in the direction of the path of travel of the radiation beam, and thus block the transmission of radiation to tissue disposed outside the tumor's spatial outline as presented to the radiation beam, dependent upon the beam's particular radial orientation with respect to the tumor volume.

Another approach to conformal radiation therapy involves the use of independently controlled collimator jaws which can scan a slit field across a stationary patient at the same time that a separate set of collimator jaws follows the target volume as the gantry of the linear accelerator rotates. An additional approach has been the use of attachments for LINACs which allow a slit to be scanned across the patient, the intensity of the radiation beam in the entire slit being modified as the slit is being scanned.

A further approach for conformal radiation therapy treatment has been the use of a narrow pencil beam of high energy photons, whose energy can be varied, and the beam is scanned over the tumor target volume so as to deliver the best possible radiation dose distribution in each orientation of the gantry upon which the photon beam source is mounted.

A major problem associated with such prior art methods of conformal radiation therapy are that if the tumor volume has concave borders, or surfaces, varying the spatial configuration, or contour, of the radiation beam, is only successful part of the time. In particular, when the convolutions, or outer surfaces, of a tumor are re-entrant, or concave, in a plane parallel to the path of the radiation treatment beam, healthy tissue or organs may be disposed within the concavities formed by the outer tumor concave surfaces, as well as the fact that the thickness of the tumor varies along the path of the radiation beam.

In order to be able to treat tumors having concave borders, it is necessary to vary the intensity of the radiation beam across the surface of the tumor, as well as vary the outer configuration of the beam to conform to the shape of the tumor presented to the radiation beam. The beam intensity of each radiation beam segment should be able to be modulated to have a beam intensity related to the thickness of the portion of the tumor through which the radiation beam passes. For example, where the radiation beam is to pass through a thick section of a tumor, the beam intensity should be higher than when the radiation beam passes through a thin section of the tumor.

Dedicated scanning beam therapy machines have been developed wherein beam intensity modulation can be accomplished through the use of a scanning pencil beam of high energy photons. The beam intensity of this device is modulated by increasing the power of its electron gun generating the beam. The power increase is directed under computer control, as the gun is steered around the tumor by moving the gantry upon which it is mounted and the table upon which the patient lies. The effect is one of progressively "painting" the target with the thickness, or intensity, of the paint, or radiation beam intensity, being varied by the amount of paint on the brush, or how much power is applied to the electron gun, as the electron gun moves over the tumor. Such dedicated scanning beam therapy machines, which utilize direct beam energy modulation, are expensive and quite time consuming in their use and operation, and are believed to have associated with them a significant patient liability due to concerns over the computer control of the treatment beam itself.

Other methods and apparatus for conformal radiation therapy have been developed that spatially modulate the beam intensity of a radiation beam across a volume of tissue in accordance with the thickness of the tumor in the volume of tissue by utilizing a plurality of radiation beam segments. Such methods and apparatus utilize attenuating leaves, or shutters, in a rack positioned within the radiation beam before the beam enters the patient. The tumor is exposed to radiation in slices, each slice being selectively segmented by the shutters. However, a minor disadvantage of that method and apparatus results from the fact that only two slices of tissue volume may be treated with one rotation of the gantry of the linear accelerator. Although the slices may be of arbitrary thickness, greater resolution is accomplished by selecting slices for treatment that are as thin as possible. As the thickness of the treatment slices decreases, the time it takes to treat the patient increases because more treatment slices are required in order to treat the entire tumor volume.

A new method and apparatus for conformal radiation therapy, for use with a radiation beam having a predetermined, constant beam intensity for treatment of a tumor has been proposed in copending Patent Application No. 08/634,785 to Mark P. Carol, filed Apr. 19, 1996, which includes a radiation beam source for producing a radiation beam having a predetermined, constant beam intensity; at least a 3×3 checkerboard array having alternating radiolucent and radiopaque compartments, for separating the radiation treatment beam into an array of a plurality of beam segments; and means for independently modulating the beam intensity of the radiation beam segments to spatially modulate the beam intensity of the radiation treatment beam across the tumor.

The foregoing methods and apparatus are designed to minimize the portion of the structures being exposed to radiation. However, because exposure to surrounding structures cannot be completely prevented, treatment plans are desired that are optimized to eradicate the tumor volume while minimizing the amounts of radiation delivered to the surrounding structures. Existing methods and apparatus for optimizing treatment plans use a computer to rate possible plans based on score functions which simulate a physician's assessment of a treatment plan. However, existing methods and apparatus have proven to be insufficient.

Existing methods and apparatus utilize a computational method of establishing optimized treatment plans based on an objective cost function that attributes costs of radiation of various portions of both the tumor and surrounding tissues, or structures. One such computational method is known in the art as simulated annealing. Existing simulated annealing methods utilize cost functions that consider the costs of under-exposure of tumor volumes relative to over-exposure of surrounding structures. However, the cost functions used in existing methods do not account for the structure volumes as a whole, relying merely on costs related to discrete points within the structure, and further do not account for the relative importance of varying surrounding structure types. For example, certain structure types are redundant in their function and substantial portions of the structure volume can be completely eradicated while retaining their function. Other structure types lose their function if any of the structure is completely eradicated. Therefore, the more sensitive structure volumes can receive a measured dose of radiation so long as no portion of the structure is subjected to a lethal dose.

Existing cost functions utilized in the optimization of treatment plans do not account for such varying costs associated with the different types of structures. After the treatment plan is optimized, the physician currently must evaluate each computed treatment plan for compliance with the desired treatment objective. If the computed treatment plan does not successfully meet the treatment objectives, the optimization process is repeated until a treatment plan can be computed that meets the physician's treatment objectives for both the tumor volume and the surrounding structures.

Further, existing methods and apparatus do not allow the physician to utilize the familiar partial volume data associated with Cumulative Dose Volume Histogram ("CDVH") curves in establishing the desired dose distributions.

Accordingly, prior to the development of the present invention, there has been no method or apparatus for conformal radiation therapy, for use with a radiation beam having a predetermined, constant beam intensity for treatment of a tumor which: are simple and economical to use; that has what is believed to be a high safety factor for patient safety; which computes an optimal treatment ID plan to meet conflicting, pre-determined, treatment objectives of a physician, accounting for objectives in both the target tumor volume and multiple structure types; and which utilizes partial volume data or the associated CDVH curves in establishing the desired dose distributions for each target tumor volume and tissue and structure types.

Therefore, the art has sought a method and apparatus for conformal radiation therapy, for use with a radiation beam having a predetermined, constant beam intensity for treatment of a tumor which: is simple and economical to use; that has what is believed to be a high safety factor for patient safety; which computes an optimal treatment plan to meet conflicting, pre-determined, treatment objectives of a physician, accounting for objectives in both the target tumor volume and multiple structure types; and which utilizes partial volume data or the associated CDVH curves in establishing the desired dose distributions for each target tumor volume and tissue and structure types.

SUMMARY OF INVENTION

In accordance with the invention, the foregoing advantages have been achieved through a method of determining an optimized radiation beam arrangement for applying radiation to a tumor target volume while minimizing radiation of a structure volume in a patient, comprising the steps of: using a computer to computationally obtain a proposed radiation beam arrangement; using a computer to computationally change the proposed radiation beam arrangement iteratively, incorporating a cost function at each iteration to approach correspondence of a CDVH associated with the proposed radiation beam arrangement to a CDVH associated with a pre-determined desired dose prescription; and rejecting the change of the proposed beam arrangement if the change of the proposed radiation beam arrangement leads to a lesser correspondence to the desired prescription and accepting the change of the proposed radiation beam arrangement if the change of the proposed radiation beam arrangement leads to a greater correspondence to the desired prescription to obtain an optimized radiation beam arrangement. The cost function may be obtained by the steps of: determining a CDVH associated with the desired dose prescription; assigning zones to each CDVH; assigning weights to each zone, applicable to the CDVHs associated with both the desired dose prescription and the proposed radiation beam arrangement; calculating a zone cost for each target and each structure, according to the following formula:

$$C_z = W_z * (A_p / A_d),$$

where $C_z$ is the cost for the current zone, $W_z$ is the weight assigned to the current zone, $A_p$ is the area or length of the current zone of the proposed CDVH, and where $A_d$ is the area or length of the current zone of the desired CDVH; calculating a target or structure cost for each target or structure, according to the following formula:

$$C_T = \Sigma C_{z1} + C_{z2} + C_{z3} + \ldots C_{zn}, \text{ and}$$

$$C_S = \Sigma C_{z1} + C_{z2} + C_{z3} + \ldots C_{zn},$$

where $C_S$ and $C_T$ are the cost for each structure or zone, and $C_{z1}$, $C_{z2}$, $C_{z3}$, and $C_{zn}$ are the costs calculated for each zone of the first, second, and third, through nth zone of each target or structure; and calculating a total cost for the change in the proposed radiation beam arrangement, according to the following formula:

$$C_{Total} = C_S + C_T,$$

where $C_{Total}$ is the total cost of the proposed change to the beam arrangement. Further, the optimized radiation beam arrangement may be applied to the patient with a conformal radiation therapy apparatus and the proposed radiation beam arrangement may be calculated using simulated annealing radiation therapy planning methods. Still further, the CDVH associated with the pre-determined dose prescription may be graphically entered into the computer, or the CDVH may be computationally constructed by the computer based on partial volume data associated with the predetermined desired dose prescription entered into the computer.

In accordance with another aspect of the invention, the foregoing advantages have been achieved through a method of determining an optimized radiation beam arrangement for applying radiation to a tumor target volume while minimizing radiation of a structure volume in a patient, comprising the steps of: (a) determining a desired CDVH associated with each target and structure; (b) using a computer to iteratively compare a cost of a radiation beam arrangement proposed during a given iteration to a beam arrangement proposed during the previous iteration based on the relative cost associated with the proposed radiation beam arrangements, the costs being calculated by: (1) determining a CDVH associated with each target and structure based on the proposed radiation beam arrangement of a given iteration; (2) assigning cost zones to the desired CDVH and the proposed CDVH of a given iteration associated with each target and structure; (3) assigning a weight value to each cost zone of each CDVH associated with each target and structure; (4) for each target and structure, multiplying the weight value of each zone by the quotient of a value representing the area of the zone of the CDVH associated with the proposed radiation beam arrangement and a value representing the area of the zone of the CDVH associated with the desired radiation beam arrangement; (5) summing the results of step (4) for each zone of each CDVH of each target and structure to obtain a total dosage cost; (c) accepting the proposed radiation beam arrangement of a given iteration if the total dosage cost of a given iteration is less than the total dosage cost of the previous iteration; (d) rejecting the proposed radiation beam arrangement of a given iteration if the total dosage cost of a given iteration is greater than the total dosage cost of the previous iteration; and (e) repeating steps b–d until the proposed radiation beam arrangement has a total dosage cost value within an acceptable level to obtain an optimized radiation beam arrangement. Further, the proposed radiation beam arrangement may be calculated using simulated annealing radiation therapy planning methods and the optimized radiation beam arrangement may be applied to the patient using a conformal radiation therapy apparatus.

In accordance with another aspect of the invention, the foregoing advantages have been achieved through a method of determining an optimized radiation beam arrangement for applying radiation to a tumor target volume while minimizing radiation of a structure volume in a patient, comprising the steps of: determining a desired CDVH for each of at least one target or structure, representing the desired cumulative effect of a radiation dose to be applied to the patient; calculating a proposed radiation beam arrangement proposed to be applied to the patient, associated with a total dosage cost; creating a proposed CDVH for each of the at least one target or structure, representing the cumulative effect of the proposed radiation beam arrangement; assigning a plurality of cost zones for each of the desired CDVHs; assigning a zone weight for each of the plurality of cost zones of each of the CDVHs; determining a zone cost value representing a zone cost for each cost zone of each CDVH of each target and structure for each of the plurality of cost zones of each of the desired CDVHs by multiplying a value representing the cost zone's zone weight by a value representing the quotient of a value representing the cost zone's zone area bounded by the proposed CDVH and a value representing the cost zone's zone area bounded by the desired CDVH; determining a total target cost value representing a cost of the proposed radiation beam arrangement for each of the at least one target by summing the zone cost values of each of the at least one target; determining a total structure cost value representing a cost of the proposed radiation beam arrangement for each of the at least one structure by summing the zone cost values of each of the at least one structure; and determining a total dosage cost value representing the total cost of the proposed radiation beam arrangement by summing each target cost value and each structure cost value. Further, in response to the total dosage cost value, the proposed dosage represented by the proposed CDVH may be applied to a patient by a conformal radiation therapy apparatus if the total dosage cost value is within an acceptable level or the dosage represented by the proposed target CDVH may be rejected if the total dosage cost value is outside an acceptable level. Still further, the proposed radiation beam arrangement may be calculated using simulated annealing radiation therapy planning methods.

In accordance with another aspect of the invention, the foregoing advantages have been achieved through an apparatus for determining an optimized radiation beam arrangement for applying radiation to a tumor target volume while minimizing radiation of a structure volume in a patient, comprising the steps of: using a computer to computationally obtain a proposed radiation beam arrangement; using a computer to computationally change the proposed radiation beam arrangement iteratively, incorporating a cost function at each iteration to approach correspondence of partial volume data associated with the proposed radiation beam arrangement to partial volume data associated with a pre-determined desired dose prescription; and rejecting the change of the proposed radiation beam arrangement if the change of the proposed radiation beam arrangement leads to a lesser correspondence to the desired prescription and accepting the change of the proposed radiation beam arrangement if the change of the proposed radiation beam arrangement leads to a greater correspondence to the desired prescription to obtain an optimized radiation beam arrangement. Further, the partial volume data may be calculated by the computer based on a CDVH graphically entered into the computer using a pointing device, or the partial volume data may be entered directly into the computer.

In accordance with another aspect of the invention, the foregoing advantages have been achieved through an apparatus for determining an optimized radiation beam arrangement for applying radiation to a tumor target volume while minimizing radiation of a structure volume in a patient, comprising: a computer, adapted to computationally obtain a proposed radiation beam arrangement, the computer further adapted to computationally change the proposed radiation beam arrangement iteratively, the computer further adapted to incorporate a cost function at each iteration to approach correspondence of partial volume data associated with the proposed radiation beam arrangement to partial volume data associated with a pre-determined desired dose prescription, and the computer may be further adapted to reject the change of the proposed radiation beam arrangement if the change of the proposed radiation beam arrangement leads to a lesser correspondence to the desired dose prescription and to accept the change of the proposed radiation beam arrangement if the change of the proposed radiation beam arrangement leads to a greater correspondence to the desired dose prescription to obtain an optimized radiation beam arrangement. The apparatus may further comprise a conformal radiation therapy apparatus in communication with the computer for applying the optimized radiation beam arrangement to the patient. Further, the partial volume data may be represented as a CDVH.

In accordance with another aspect of the invention, the foregoing advantages have been achieved through an apparatus for determining an optimized radiation beam arrangement for applying radiation to a tumor target volume while minimizing radiation of a structure volume in a patient, comprising a computer, including: means for computationally obtaining a proposed radiation beam arrangement, means for computationally changing the proposed radiation beam arrangement iteratively, means for incorporating a cost function at each iteration to approach correspondence of partial volume data associated with the proposed beam arrangement to partial volume data associated with a predetermined desired dose prescription, and means for rejecting the change of the proposed radiation beam arrangement if the change of the proposed beam arrangement leads to a lesser correspondence to the desired prescription and accepting the change of the proposed radiation beam arrangement if the change of the proposed radiation beam arrangement leads to a greater correspondence to the desired prescription to obtain an optimized radiation beam arrangement. Further, the apparatus may further comprise a conformal radiation therapy apparatus in communication with the computer for applying the optimized radiation beam arrangement to the patient. Further, the partial volume data may be represented as a CDVH.

In accordance with another aspect of the invention, the foregoing advantages have been achieved through a method of determining an optimized radiation beam arrangement for applying radiation to at least one tumor target volume while minimizing radiation of at least one structure volume in a patient, comprising the steps of: determining desired partial volume data for each of the at least one target volume and structure volume associated with a desired dose prescription; entering the desired partial volume data into a computer; in response to the desired partial volume data, using the computer to computationally approximate desired CDVHs for each of the at least one target and structure associated with the desired dose prescription; and using the computer to computationally calculate the optimized radiation beam arrangement associated with the CDVHs approximated by the computer. Further, the CDVHs may be approximated by the steps of: using the computer to computationally obtain a set of proposed beam weights; using the computer to computationally change the set of proposed beam weights iteratively, incorporating a cost function at each iteration to determine a cost of the change to the set of proposed beam weights; and rejecting the change to the set of proposed beam weights if the change to the set of proposed beam weights leads to a lesser correspondence to the desired CDVHs and accepting the change to the set of proposed beam weights if the change to the set of proposed beam weights leads to a greater correspondence to the desired CDVHs. Still further, the optimized radiation beam arrangement may be calculated using simulated annealing radiation therapy planning methods, the optimized radiation beam arrangement may be applied to the patient with a conformal radiation therapy apparatus, and the desired CDVHs may be computationally constructed by the computer based on numerical values representing the partial volume data entered into the computer.

In accordance with another aspect of the invention, the foregoing advantages have been achieved through a method of determining an optimized radiation beam arrangement for applying radiation to at least one tumor target volume while minimizing radiation of at least one structure volume in a patient, comprising the steps of: distinguishing each of the at least one tumor target volume and each of the at least one structure volume by target or structure type; determining desired partial volume data for each of the at least one target volume and structure volume associated with a desired dose prescription; entering the desired partial volume data into a computer; in response to the desired partial volume data and in response to the target or structure type of each of the at least one tumor target volume and each of the at least one structure volume, using the computer to computationally calculate an optimized radiation beam arrangement. Further, the optimized radiation beam arrangement may be applied to the patient with a conformal radiation therapy apparatus.

The planning method and apparatus for radiation dosimetry, when compared with previously proposed prior art methods and apparatus, have the advantages of: being simple and economical to use; having what is believed to be a high safety factor for patient safety; computing an optimal treatment plan to meet conflicting, pre-determined, treatment objectives of a physician, accounting for objectives in both the target tumor volume and multiple tissue structure types, and utilizing CDVH curves in establishing the optimal beam arrangements to achieve the desired dose distributions for each target tumor volume and tissue and structure types.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as to be defined by claims to be filed in a non-provisional application.

DETAILED DESCRIPTION OF THE INVENTION

Simulated annealing radiotherapy planning ("SARP") methods are well known in the art to compute optimized radiation beam arrangements to meet objective parameters of a physician with regard to conflicting treatment objectives of a tumor volume and its surrounding structures. Existing SARP methods utilize systematic algorithms to calculate a proposed, optimized beam arrangement. Modern LINACs radiate a tumor site by making multiple passes along varying arcs approaching the target volume along different entrance paths, each arc being directed toward a point central to a target volume, commonly referred to as an epicenter of the treatment volume. Each pass of the treatment beam will radiate the portions of the tumor and surrounding structures passing within that arc. By utilizing such multiple beam passes, certain portions of the treatment field are irradiated by only some of the beam arcs while other portions of the treatment field are radiated by each beam arc, thereby causing the highest dose concentration to occur at the epicenter.

Figure 6A:
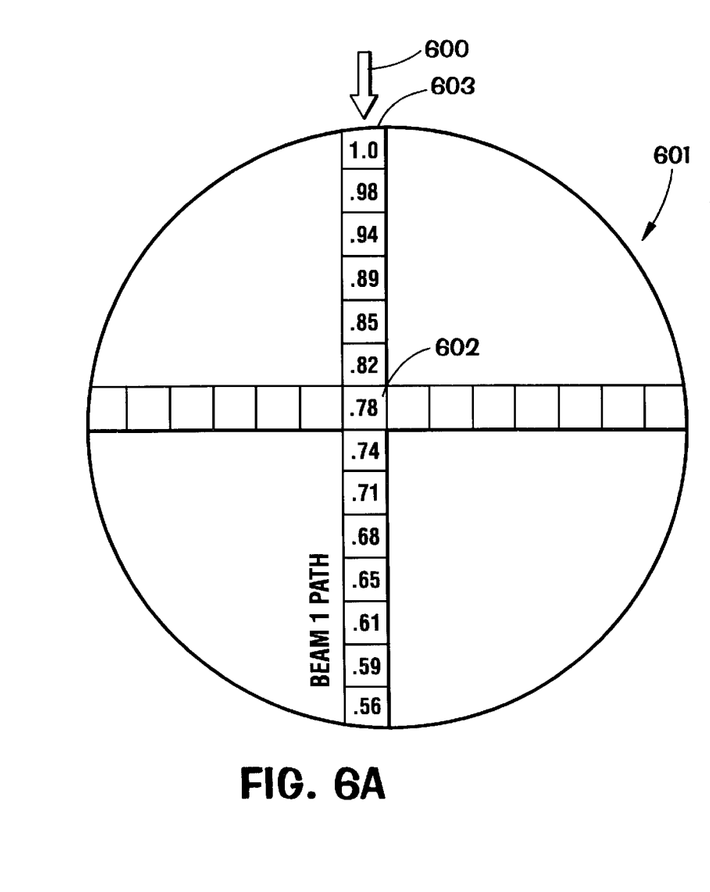
FIG. 6A is a dose treatment, showing the dose relationship of a single treatment beam passing through a treatment field.
Figure 6B:
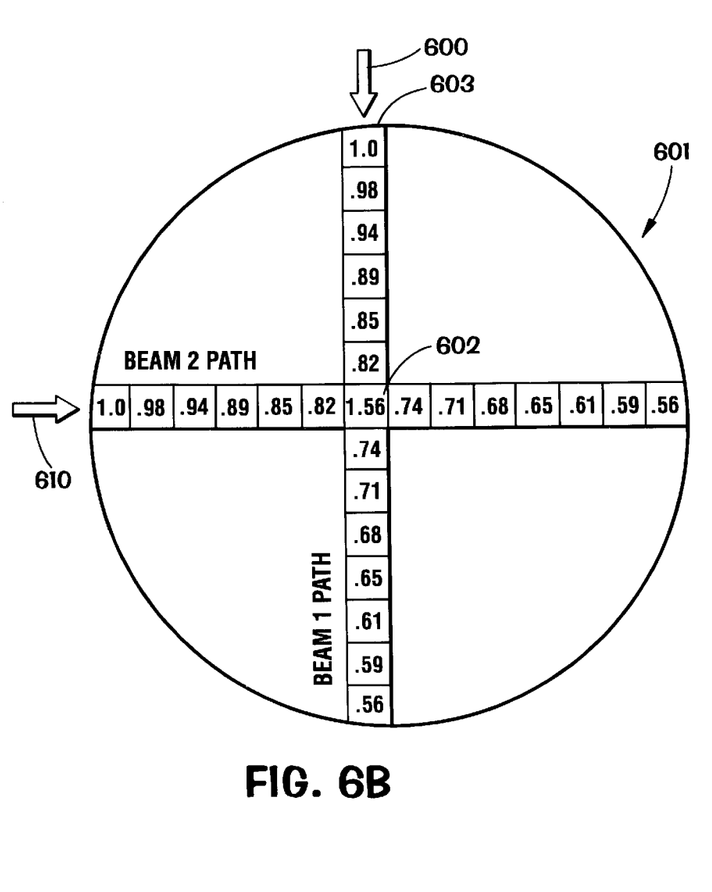
FIG. 6B is a dose treatment, showing the dose relationship of two beams passing through a treatment field.

Referring to FIGS. 6A and 6B, by way of example, FIG. 6A shows a dose relationship for the central ray of a single beam directed toward a treatment field from the direction indicated by arrow 600. The three-dimensional treatment field is shown projected on the two-dimensional grid 601. In this example, if a single beam is used, the beam weight, or intensity, at the epicenter 602 would be 78% of the dose at the entrance point 603. If a second beam of equal intensity were directed toward the treatment field from the direction indicated by arrow 610 (FIG. 6B) and placed so that the two beams intersected only at the epicenter 602, the dose at the epicenter 602 would be two times 78%, or 156% of the dose from each respective treatment beam. The cumulative effect of multiple beams passing through the treatment field from the different entrance paths 600, 610 thereby creates a concentration of dose to occur at the epicenter 602.

The optimizer of the present invention computes an optimized treatment plan, or beam arrangement, which should be understood to include either the optimal beam positions around the treatment field, the optimal array of beam weights, or beam intensities, otherwise known as an intensity map or a fluence profile or both. The optimal beam arrangement is arrived at by computationally increasing the proposed beam weight iteratively, incorporating cost functions to ensure that an iterative change in the beam weight would not result in an unacceptable exposure to the volumes of tissue or other structures being subjected to the proposed dose. At each iteration, the dose distribution resulting from the proposed beam selection is compared to a prescribed dose for the tumor volume and surrounding tissue structures. If the increase or decrease in beam weights would lead to a greater correspondence to the desired prescription, the change is accepted. Ultimately, the SARP method will produce an optimized treatment plan, based on the treatment objectives as expressed by the cost function incorporated in the SARP algorithm.

Figure 1:
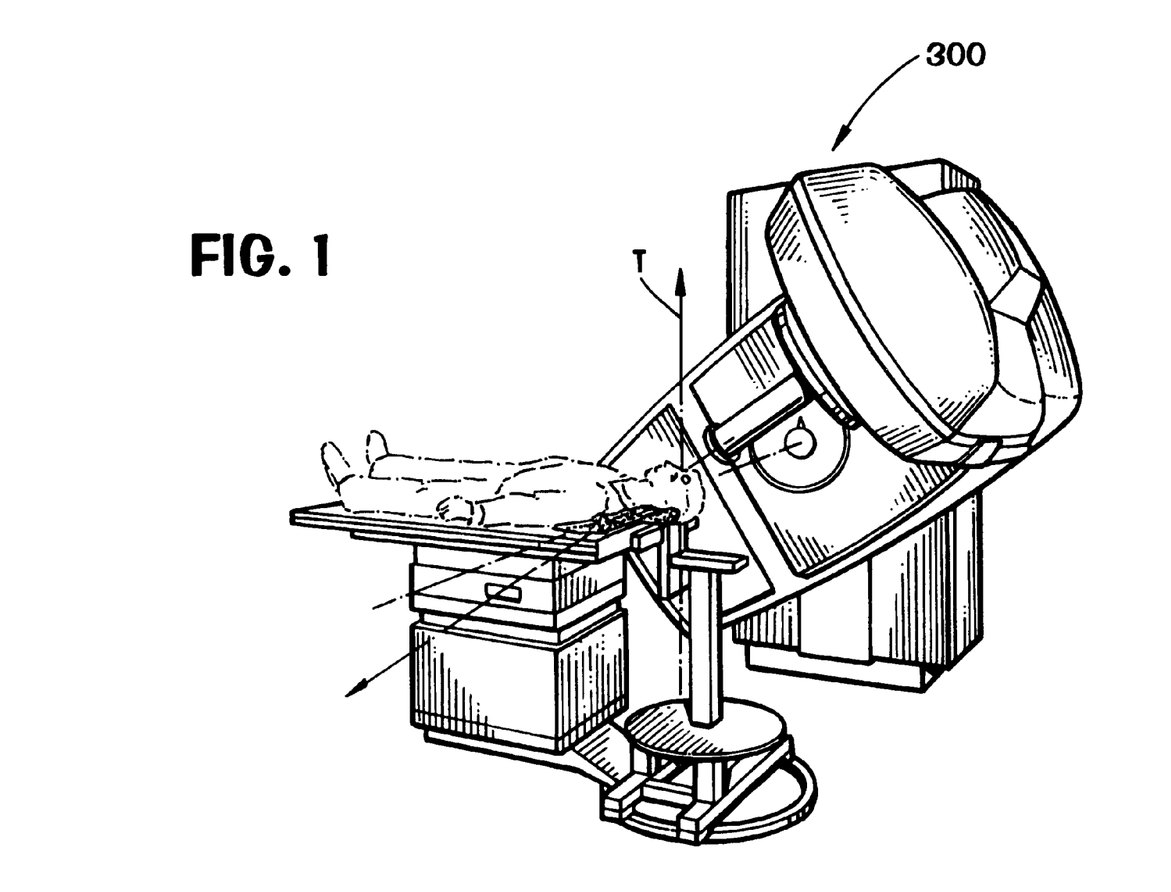
FIG. 1 is a perspective view of a conventional linear accelerator, including a rotatable couch, collimator and gantry.

The system of the present invention includes an improved optimized treatment planning system, which accounts for multiple treatment parameters for both a target and multiple surrounding structure types. The system includes a modified cost function, which allows a physician to use conventional cumulative dose volume histographs ("CDVH"s) to establish a desired prescription of dosage to both the target volume, or target, and each involved structure volume, or structure, which will then be used as input for the system for determining the proposed radiation dose distribution for delivery to a patient. The optimization method may be carried out using conventional equipment, including a conventional linear accelerator ("LINAC") 300, as shown in FIG. 1, having a rotatable gantry, a conventional computer or set of computers, and plan optimization software, which utilizes the optimization method of the present invention.

Figure 2:
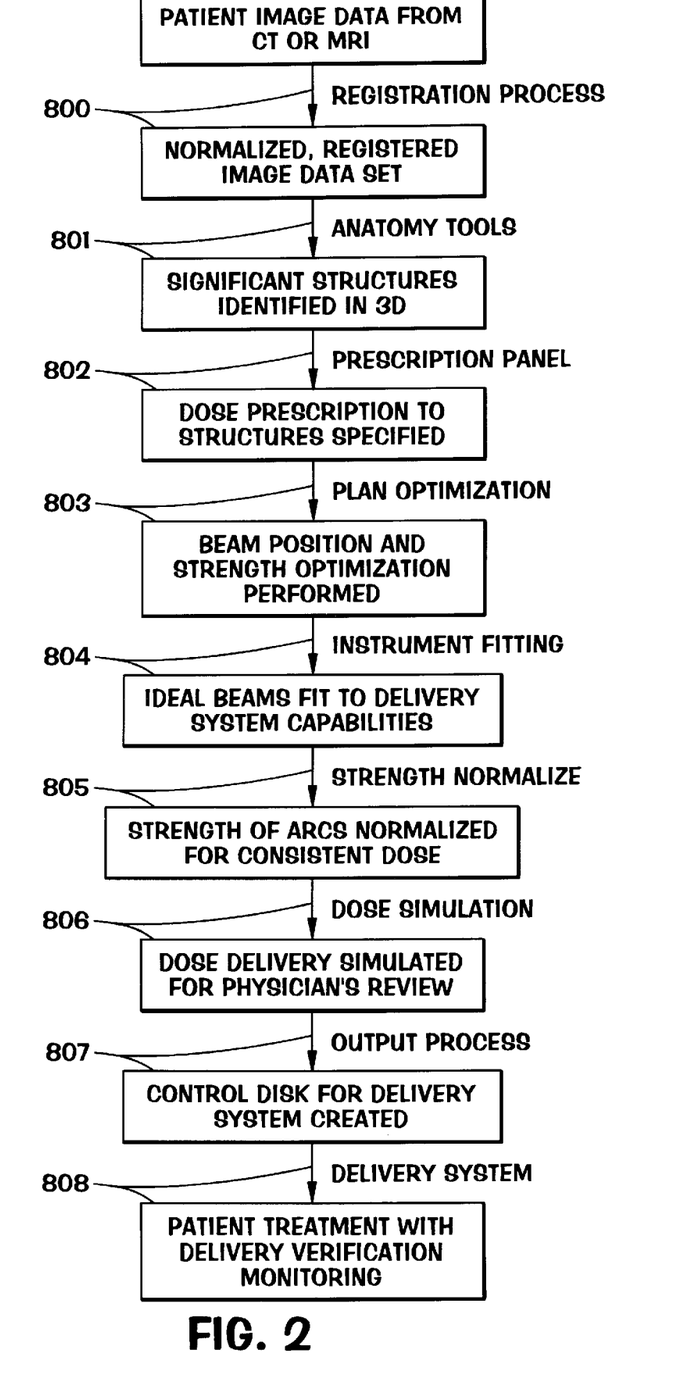
FIG. 2 is a flow diagram of a radiation planning system for controlling the operation of the apparatus of the present invention.

FIG. 2 shows a procedure for creating a treatment plan utilizing the system of the present invention. The first step of the method is generally referred to as the Registration Process step 800. This is the process step of aligning a set of conventional axial slice images of the portion of the patient to be treated by the conformal radiation therapy of the present invention. These images are first obtained by conventional computerized tomographic ("CT") scanning or magnetic resonance imaging ("MRI") techniques which produce an image representing a "slice" of tissue displayed with anatomical accuracy. The series of "slices", which constitute the complete CT or MRI study, represents a three-dimensional picture of a particular portion of the patient, to allow visualization as a valid three-dimensional data set. The resulting data is achieved by sampling the input data, determining common marks of known geometry, and warping the data to be correctly aligned. Resulting resolution is set so that it is geometrically correct based on the known patient fixation device utilized, as previously described, and if images have been scanned from film, gray scale image normalization is done based on reference graybars including in the images. Conventional two-dimensional image warping techniques are utilized, with super sampling and filtering as required for resolution adjustment. Image slice spacing is entered by the operator of the planning system and verified by the known patient fixation device geometry.

The next step of the system is generally referred to as the Anatomy Tools step 801. The physician identifies the three-dimensional volume of the structure significant to radiation planning, in a conventional manner, whereby the physician identifies anatomical structures on an image slice-by-slice basis.

The Prescription Panel step 802 allows the physician to input into the planning system the desired goal of the radiation therapy treatment, which is utilized in the plan optimization step 803.

Figure 3:
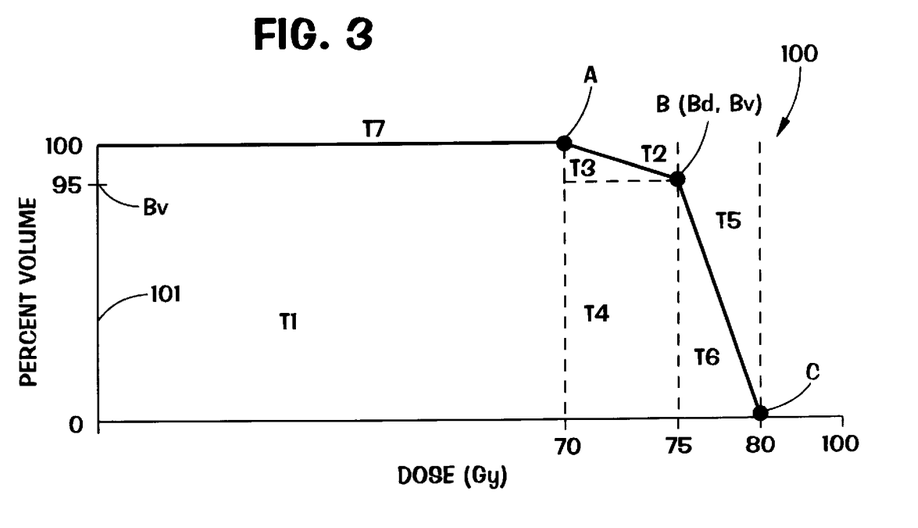
FIG. 3 is a target CDVH curve used in the system of the present invention.
Figure 4:
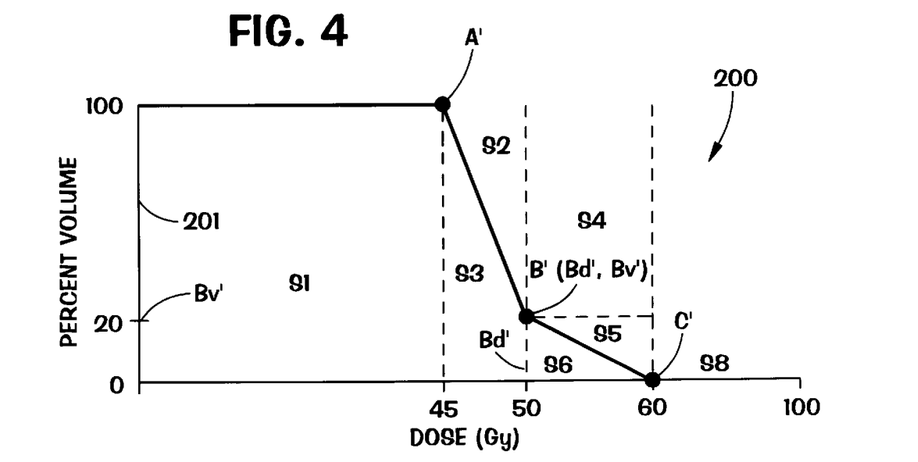
FIG. 4 is a structure CDVH curve used in the system of the present invention.

FIGS. 3 and 4 show conventional target and structure CDVH curves 100, 200, respectively, which are typically used by a physician in reviewing the effect a given dose distribution will have on a target or structure before that dose distribution is applied to the patient. Physicians and those skilled in the art of radiation dosimetry are familiar with CDVH curves 100, 200; however, they are typically used to analyze a dose distribution after a treatment plan has been optimized. In contrast, the familiar CDVH curves 100, 200 are used by a physician using the system of the present invention not only in the Output Process step 807 (FIG. 2), discussed hereinafter in detail, but also prior to the Plan Optimization step 803 (FIG. 2) to establish partial volume data representing dosage limits and other parameters, as hereinafter discussed in detail, for each target and structure to establish the input parameters for the cost function of the present invention, which may be entered in the Prescription Panel step 802 (FIG. 2) of the present invention.

Figure 5A:
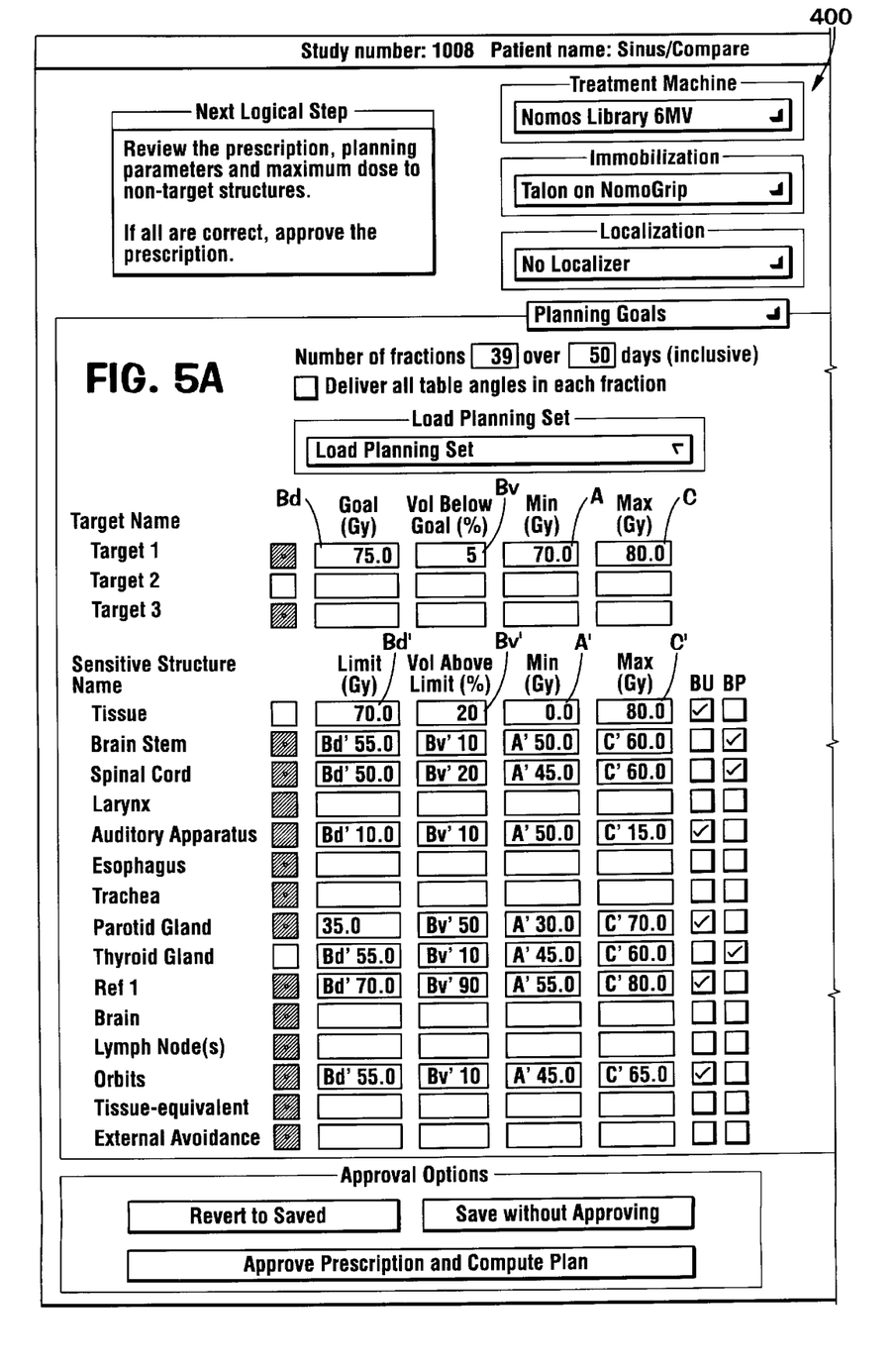
FIG. 5 is a prescription panel of the system of the present invention.
Figure 5B:
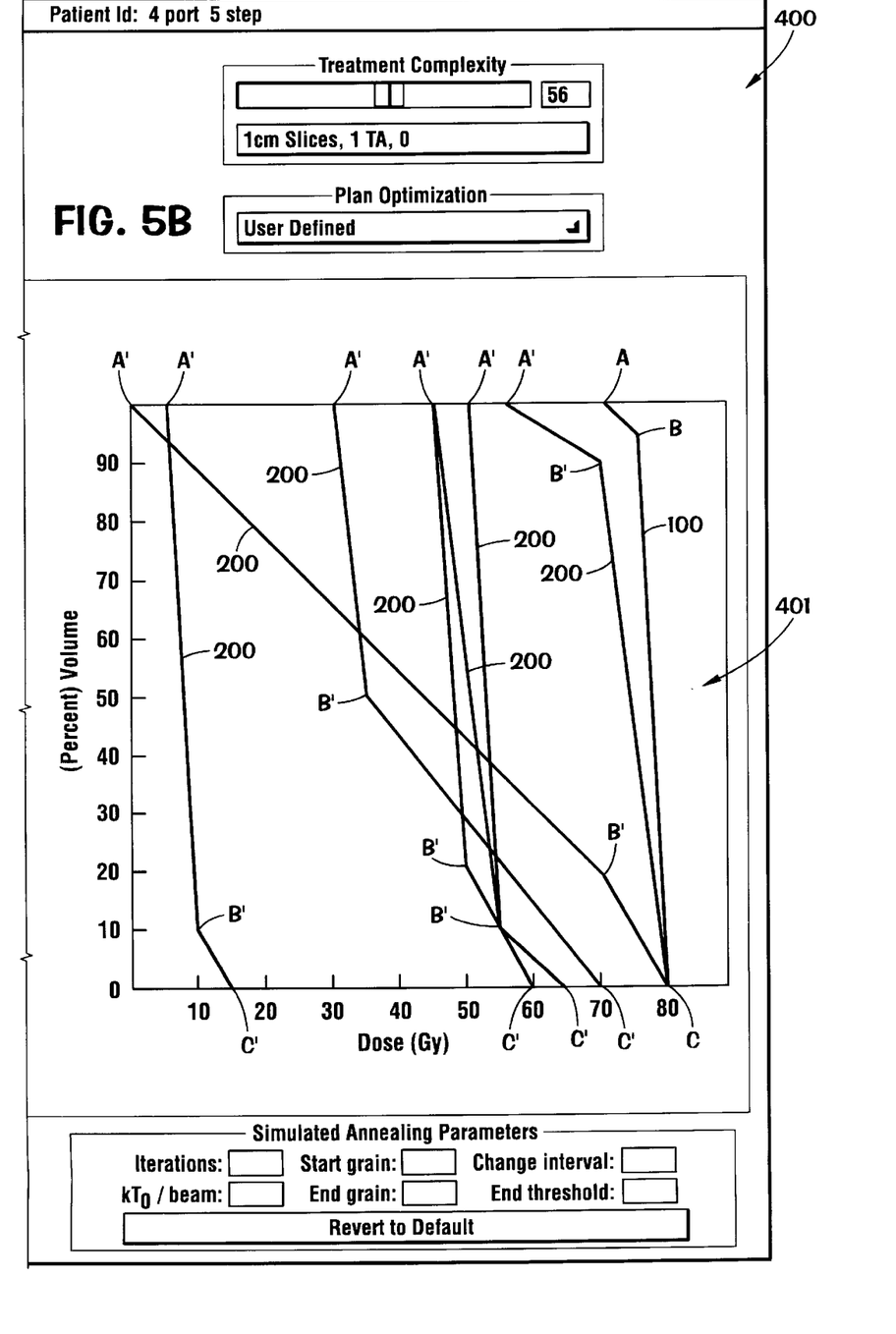

The CDVH curves 100, 200 utilized in the system of the present invention are created from partial volume data for each target and structure of a given patient. In the system of the present invention, partial volume data are entered by the user during the Prescription Panel step 802 (FIG. 2). FIG. 5 shows an embodiment of a prescription panel 400 used to input the partial volume data into the planning system of the present invention. The partial volume data generally describes what percent of the volume of a tumor or structure can receive how much dose. With reference now to FIG. 3, the partial volume data for a target may include data corresponding to values represented as data points on a target CDVH curve 100. The target dosage goal value Bd is the desired dose to be achieved in the target volume; the target maximum dosage value C is the maximum dose to be received by any portion of the target; the target minimum dosage value A is the minimum dose to be received by any portion of the target volume that will be underdosed; and the portion of the target volume which should have a dose greater than the goal may be represented by target percent over goal value Bv. The target dosage goal value Bd and target percent over goal value Bv comprises the co-ordinates of the data point B.

An illustrative target CDVH curve 100 is shown in FIG. 3. By way of example, a physician may determine that a given target volume must receive less than 80 Gy. Therefore, the target maximum dose value C would be 80 Gy, whereby no portion of the target volume could receive a cumulative dose of 80 Gy. Next, the physician may determine that the desired cumulative dose to the target volume should be 75 Gy and, that only five (5%) percent of the target volume should receive a cumulative dose less than 75 Gy. Therefore, ninety-five (95%) percent of the target volume should receive a cumulative dose greater than 75 Gy. Accordingly, the target dosage goal Bd would be 75 Gy and the target percent over goal value Bv would be ninety-five (95%) percent. Finally, the physician may determine that the entire target should receive a minimum dosage value of 70 Gy. Therefore, the target minimum dosage value A would be 70 Gy. The target CDVH curve 100 created when plotting these values as a conventional CDVH curve is shown in FIG. 3. After the physician has input the desired target goals into the system according to the Prescription Panel step 802 (FIG. 2), the system of the present invention may display the corresponding target CDVH curve 100 for review by the physician. Alternatively, the physician may be able to draw the target CDVH curve 100 graphically using a mouse or other pointing device and the system would then present the numeric values representing the target goals corresponding to the target CDVH curve 100.

Referring now to FIG. 4, an illustrative structure CDVH 200 is shown. By way of example, the partial volume data for a structure may include data corresponding to values represented as data points on a structure CDVH curve 200. The structure dosage limit value Bd' is the desired dosage limit not to be exceeded in the volume of a sensitive structure; the structure maximum dosage value C' is the maximum dose to be received by any portion of the structure; the structure minimum dosage value A' is the dose below which there is no appreciable benefit gained by reducing the exposure to the structure; and the portion of the structure volume which can have a dose greater than the goal dosage may be represented by structure percent over limit value Bv'. The structure dosage limit value Bd' and structure percent over limit value Bv' comprise the co-ordinates of the data point B'.

An illustrative structure CDVH curve 200 is shown in FIG. 4. By way of example, a physician may determine that a given structure volume must receive less than 60 Gy. Therefore, the structure maximum dose value C' would be 60 Gy, whereby no portion of the structure volume can receive a cumulative dose of 60 Gy. Next, the physician may determine that the desired cumulative dose limit to the structure volume should be 50 Gy and that only twenty (20%) percent of the structure volume should receive more than this cumulative dose. Therefore, eighty (80%) percent of the structure volume should receive a cumulative dose less than 50 Gy. Accordingly, the structure dosage limit Bd' would be 50 Gy and the structure percent over goal value Bv' would be twenty (20%) percent. Finally, the physician may determine that there is no appreciable benefit gained by reducing the exposure to the structure below 45 Gy. Therefore, the structure minimum dosage value A would be 45 Gy. The structure CDVH curve 200 created when plotting these values as a conventional CDVH curve is shown in FIG. 4. After the physician has input the desired structure goals into the system according to the Prescription Panel step 802 (FIG. 2), the system of the present invention may display the corresponding target and structure CDVH curves 100, 200 for review by the physician. Alternatively, the physician may be able to draw the target and structure CDVH curves 100, 200 graphically using a mouse or other pointing device and the system would then present the numeric values representing the target goals corresponding to the CDVH curves 100, 200. In any event, the resulting CDVH curves for both the target and the structures can be compared to ensure that the structure curves fit within the bounds of the target curves. This can be accomplished by overlaying the graphs manually or, in a preferred embodiment, by simultaneously displaying the graphs alongside the numerical representations of the partial volume data, as shown in FIG. 5.

FIG. 5 shows an embodiment of a prescription panel 400 used in the Prescription Panel step 802 of the present invention in which numerical values are entered for the partial volume data for each target and structure. The corresponding target and structure CDVH curves 100, 200 are displayed in a graphical window 401.

In the Plan Optimization step 803, the radiation plan optimization is a specific case of an inverse problem, where the goal is to determine the best way to achieve the dose prescription. A SARP technique is utilized to do this optimization by dividing the radiation delivery into a large number of small beams, each of which hit the target. The annealing cooling schedule utilized, fits into the class of FSA (Fast Simulated Annealing) techniques. Except for the foregoing detailed description of the cost function utilized in the present system, the details of the foregoing simulated annealing techniques are known in the art and are described in such publications as "Optimization of Conformal Radiotherapy Dose Distributions by Simulated Annealing", S. Webb, Physics and Medical Biology, Vol. 34, PP. 1349–1370 (1989); and "Optimization of Conformal Radiotherapy Dose Distributions by Simulated Annealing: 2. Inclusion of Scatter in the 2d Technique", S. Webb, Physics and Medical Biology, vol. 36, pp. 1227–1237, (1991), which publications are incorporated herein by reference. A suitable computer is utilized in performing the Plan Optimization step, as well as the other steps of the radiation planning system.

Referring again to FIGS. 3 and 4, utilizing familiar target and volume CDVH curves such as target and volume CDVH curves 100, 200 (FIGS. 3 and 4), certain regions or zones of the CDVH curves may be identified as being more important for a particular type of target or structure. Relative weights are then assigned by the computer, after experimental generation by the user that will achieve the desired objective of each type of target or structure when applied by the cost function of the present invention, as further described below. In a preferred embodiment, target volume CDVH curve 100 (FIG. 3) comprises seven zones T1–T7. Zones T1–T6 represent areas above and below the target volume CDVH curve 100, while zone T7 represents the length of the line extending from the axis 101, representing the target volume, to the data point A, representing the target minus dosage value. Similarly, with reference now to FIG. 4, structure volume CDVH curve 200 (FIG. 4) may also comprise seven zones S1–S6, and S8. Zones S1–S6, and S8 each representing the respective areas above and below the structure CDVH curve 200.

The cost function is an analytical determination of whether, when any change is made to the strengths of the beams being used to treat the patient, the resultant dose distribution is closer to the result desired by the user. In the cost function of the present invention, each region, or zone, of the CDVH is assigned a relative weight, according to the importance of that region, or zone, of the CDVH. A zone cost is then calculated for the target and each structure, according to the following formula:

$$C_z = W_z * (A_p/A_d),$$

where $C_z$ is the cost for the current zone, $W_z$ is the weight assigned to the current zone, $A_p$ is the area of the current zone of the proposed CDVH curve, or pseudo-curve, and where $A_d$ is the area of the current zone of the desired CDVH curve except for target zone T7, where Ad is the length represented by target zone T7 and structure zone S8, where Ad is the length represented by structure zone S8. After each zone cost is calculated, the target or structure cost is calculated for each target or structure, according to the following formula:

$$C_T = \Sigma C_{z1} + C_{z2} + C_{z3} + \ldots C_{zn}, \text{ and}$$

$$C_S = \Sigma C_{z1} + C_{z2} + C_{z3} + \ldots C_{zn},$$

where $C_S$ and $C_T$ are the cost for each structure or zone, and $C_{z1}$, $C_{z2}$, $C_{z3}$, and $C_{zn}$ are the costs calculated for each zone of the first, second, and third, through nth zone of each target or structure. The total cost for the change to the proposed beam distribution is then calculated, according to the following formula:

$$C_{Total} = C_S + C_T,$$

where $C_{Total}$ is the total cost of the proposed change to the beam distribution.

In other words, if the region under the proposed CDVH curve, or pseudo-curve, is greater than the region under the desired CDVH curve, there is a high cost associated with the change to the proposed beam distribution. Thus, the system will reject the change that was made to the beams and will again attempt to change the beam weights to lower the total cost, according to conventional optimization techniques known in the art. Where target goals and structure limits conflict, beam changes will decrease the cost in the target while increasing the cost in one or more of the structures. A determination of whether or not that beam change is kept by the system depends upon the relative changes in the costs of the targets and structures.

By assigning different weights to different zones of the CDVH curves, different results can be obtained. Therefore, the weights are incorporated into the software with an outcome in mind, and the user must understand what kind of results the assigned weights will produce. One skilled in the art will be able to choose the desired weights without undue experimentation to achieve a desired outcome in the system. For instance, in one implementation of the invention, sparing of sensitive structures is preferred over treating the entire target in order to avoid complications which can result from the delivery of radiation. Sparing of sensitive structures is accomplished by delivering a dose distribution whereby the proposed structure CDVH curve, or structure pseudo-curve is equivalent to or better than the desired structure CDVH curve. In order to achieve this result, weights must be picked so that if a beam change is made that improves the proposed target CDVH curve, or target pseudo-curves, but worsens the proposed structure CDVH curves, or structure pseudo-curves, the change will be rejected. Therefore, high weights should be assigned to the structure zones that have been determined to be at risk for structural injury, such as zones S4, S5, and S8. The actual weights assigned are based upon clinical experience by one skilled in the art. These weights can then be programmed into the system so they can be used repeatedly to produce a desired outcome.

Clinical experience has shown that there are two types of structures, each category of which responds differently to radiation. For certain types of structures, maximum dose received by any part of the structure is the primary factor in determining whether or not a complication occurs. An example of such a structure, which can be called a biologically polymorphic structure ("BP structure"), is the spinal cord. In such a structure, each portion of the structure serves a distinct function; if any portion of the structure, no matter how small, is destroyed, the overall function of the structure is affected. By way of analogy, the BP type of structure can be viewed as a serial circuit. If any portion of the BP structure, no matter how small, is interrupted the circuit no longer functions. By use of a similar analogy, the BP structure is in contrast to a biologically uniform structure ("BU structure"), which can be viewed as a parallel circuit, where all portions of the BU structure perform the same function. Overdosing one portion of the BU structure with a lethal dose to that portion of the BU structure may be acceptable as long as a sufficient portion of the BU structure is preserved.

For a BP structure, zones S4, S5, and S8 may be chosen as important, with zone S8 representing the maximum dose received by any portion of the structure being chosen as the most important zone for that type of structure. For a BU structure, where maximum dose is not important as long as the desired volume of structure falls under the chosen limit, only zone S4 may be important. Thus, high weights are chosen for zones S4, S5, and S8 in BP structures. Similarly, high weights may be chosen for BU structures only in zone S4.

The effect of the distinction between BP structures and BU structures can be shown where there is a single target and a single structure. A change may be made to a beam which causes a reduction to the target cost. This beam change may cause the area in zone S5 of the CDVH curve for the structure to increase. If the structure is a BU structure, then there is no increase in total cost associated with the beam change because zone S5 in the BU structure has been assigned a very low relative weight. Therefore, the system will accept that beam change. However, if the structure is a BP structure, then there is an increase in total cost associated with the beam change because zone S5 in the BP structure has been assigned a high relative weight. In such a case, the system will not accept the beam change that caused the increase in the total cost associated with the beam change and the system will attempt another beam change to reduce the total cost for the beam distribution.

For both BP structures and BU structures, it would be desirable to obtain a beam distribution that results in a more favorable CDVH curve for each structure than the desired CDVH curve for those structures, if that is possible while still achieving target goals. Therefore, the zones to the left of the desired CDVH curves (zones S1 and S3) would also be assigned positive weights, although these weights would be relatively small. Such a weight selection would cause the system to select beam changes that would push these zones of the proposed CDVH curve left of the desired CDVH curve for those structures so long as the beam changes do not increase the cost associated with that beam change to the target.

In a particular application, it may also be desired that all targets will receive their goals regardless of the dose delivered to the structures. However, it also may be desired that the dose to the structures be limited so long as such structure dose limitations do not interfere with the ability to maximally treat the target. In this application, high weights may be assigned to zones T1, T3, and T7 in the target. The relative weights are then assigned so that they are high enough to insure that target goals will be met but not so high that the effect of the dose to the structures is ignored completely.

The weights can then be chosen through experience and minimal experimentation by one skilled in the art so that the following treatment objectives can be met in a desired application depending on the aggressiveness of the treatment plan: In one application wherein the system is biased to protect the structures, the weights can be selected that will insure that all structure limits will be met while at the same time allowing target goals to be achieved where possible; in another application wherein the system is biased to treat the target, the weights can be selected that will insure that all target goals will be met while simultaneously allowing structure limits to be achieved, where possible; In a third application, weights can be adjusted by the system to bias the beam changes based on a sliding scale between the preceding applications. A user can instruct the system to bias the beam distribution according the desired application. In the case of the third application addressed above, a value between, for example, 0 and 10, arbitrarily having a value of 0 representing achievement of target goals and a value of 10 representing preservation of structures, can be entered by the user so that beam weights are assigned according to the desired result. For example, a selection of 5 can be chosen by the user so that weights are assigned by the system to bias the system equally between treating the target volume and preserving the structure volumes. A selection of 3 would then bias the system toward treating the target volume while a selection of 7 would bias the system toward preserving the surrounding structures. The cost function of the present invention may be easily incorporated into existing SARP algorithms by one skilled in the art.

With reference again to FIG. 2, the next step in the planning system is the Instrument Fitting step 804. The resulting optimized set of radiation beam positions and beam weights, or beam intensities for the radiation beam segments, is fitted into the delivery capabilities of the LINAC apparatus 300 (FIG. 1), after optimization. An iterative process is utilized to account for OF adjustments (Output Factor), the timing of the movement of members, and limitations of simultaneous movements to arrive at control information for the LINAC apparatus 300 (FIG. 1) that represent the optimized plan and can be delivered within the operating limitations of the LINAC apparatus 300 (FIG. 1).

A Strength Normalize step 805 further normalizes the arcs of rotation through which the radiation beam source travels to insure that the tumor receives a consistent radiation dose from each position selected in order to eliminate what are known as "hot" or "cold" regions in the tissue volume being treated. This step may be done by varying the radiation dose rate of the radiation source, and may be accomplished by use of a conventional, simple linear scaling technique.

In the Dose Simulation step 800 the radiation dose to the patient is simulated based upon the control information for LINAC apparatus 300 (FIG. 1). The algorithm used in this step is based upon the Three-Dimensional Modified Path Length technique, as is known in the art. Examples of this algorithm are discussed in the following publications: "Algorithm for Dosimetry of Multiarc Linear Accelerator Stereotactic Radiosurgery", G. Luxton et al., Medical Physics, vol. 18, pp. 1211–1221 (1991); "Dosage Calculations in Radiation Therapy", W. L. Saylor, published by Urban & Schwarzenberg (1979), which publications are incorporated herein by reference.

The Output Process step 807 permits the physician to review the simulated radiation dose information and to approve the radiation plan for patient delivery. After such review and approval, a floppy disk is generated containing the data to control LINAC apparatus 300 (FIG. 1) for the specific radiation delivery case. The data includes instructions for the timing and movement of members, radiation source setup information, and conventional patient information. After the foregoing steps have been accomplished, the Delivery System step 808 is accomplished, wherein the method steps of the conformal radiation therapy method of the present invention are performed as previously described, in order to treat the tumor in the patient.

What is claimed is:

1. A method of determining an optimized radiation beam arrangement for applying radiation to a tumor target volume while minimizing radiation of a structure volume in a patient, comprising the steps of:

using a computer to computationally obtain a proposed radiation beam arrangement;

using a computer to computationally change the proposed radiation beam arrangement iteratively, incorporating a cost function at each iteration to approach correspondence of a CDVH associated with the proposed radiation beam arrangement to a CDVH associated with a predetermined desired dose prescription; and rejecting the change of the proposed radiation beam arrangement if the change of the proposed radiation beam arrangement leads to a lesser correspondence to the desired prescription and accepting the change of the proposed beam arrangement if the change of the proposed beam arrangement leads to a greater correspondence to the desired dose prescription to obtain an optimized radiation beam arrangement.

2. The method of claim 1 wherein the cost function is obtained by the steps of:

determining a CDVH associated with the desired dose prescription;

assigning zones to each CDVH;

assigning weights to each zone, applicable to the CDVHs associated with both the desired dose prescription and the proposed radiation beam arrangement;

calculating a zone cost for each target and each structure, according to the following formula:

$$C_z = W_z^* (A_p / A_d),$$

where $C_z$ is the cost for the current zone, $W_z$ is the weight assigned to the current zone, $A_p$ is the area or length of the current zone of the proposed CDVH, and where $A_d$ is the area or length of the current zone of the desired CDVH;

calculating a target or structure cost for each target or structure, according to the following formula:

$$C_T = \Sigma C_{z1} + C_{z2} + C_{z3} + \ldots C_{zn}, \text{ and}$$

$$C_S = \Sigma C_{z1} + C_{z2} + C_{z3} + \ldots C_{zn},$$

where $C_S$ and $C_T$ are the cost for each structure or zone, and $C_{z1}$, $C_{z2}$, $C_{z3}$, and $C_{zn}$ are the costs calculated for each zone of the first, second, and third, through nth zone of each target or structure; and calculating a total cost for the change in the proposed radiation beam arrangement, according to the following formula:

$$C_{Total} = C_S + C_T,$$

where $C_{Total}$ is the total cost of the proposed change to the radiation beam arrangement.

3. The method of claim 1, wherein the proposed radiation beam arrangement is calculated using simulated annealing radiation therapy planning methods.

4. The method of claim 1, wherein the proposed radiation beam arrangement is changed by changing the beam weights.

5. The method of claim 2, wherein the proposed radiation beam arrangement is calculated using simulated annealing radiation therapy planning methods.

6. The method of claim 1, further comprising the step of applying the optimized radiation beam arrangement to the patient with a conformal radiation therapy apparatus.

7. The method of claim 2, further comprising the step of applying the optimized radiation beam arrangement to the patient with a conformal radiation therapy apparatus.

8. The method of claim 3, further comprising the step of applying the optimized radiation beam arrangement to the patient with a conformal radiation therapy apparatus.

9. The method of claim 5, further comprising the step of applying the optimized radiation beam arrangement to the patient with a conformal radiation therapy apparatus.

10. The method of claim 1, wherein the CDVH associated with the pre-determined desired dose prescription is computationally constructed by the computer based on partial volume data associated with the pre-determined desired dose prescription entered into the computer.

11. The method of claim 1, wherein the CDVH associated with the pre-determined desired dose prescription is graphically entered into the computer.

12. The method of claim 2, wherein the CDVH associated with the pre-determined desired dose prescription is computationally constructed by the computer based on partial volume data associated with the pre-determined desired dose.

13. The method of claim 2, wherein the CDVH associated with the pre-determined desired dose prescription is graphically entered into the computer.

14. A method of determining an optimized radiation beam arrangement for applying radiation to a tumor target volume while minimizing radiation of a structure volume in a patient, comprising the steps of:

(a) determining a desired CDVH associated with each target and structure;

(b) using a computer to iteratively compare a cost of a radiation beam arrangement proposed during a given iteration to a radiation beam arrangement proposed during the previous iteration based on the relative costs associated with the proposed radiation beam arrangement, the costs being calculated by:

(1) determining a CDVH associated with each target and structure based on the proposed radiation beam arrangement of a given iteration;

(2) assigning cost zones to the desired CDVH and the proposed CDVH of a given iteration associated with each target and structure;

(3) assigning a weight value to each cost zone of each CDVH associated with each target and structure;

(4) for each target and structure, multiplying the weight value of each zone by the quotient of a value representing the area of the zone of the CDVH associated with the proposed radiation beam arrangement and a value representing the area of the zone of the CDVH associated with the desired radiation beam arrangement;

(5) summing the results of step (4) for each zone of each CDVH of each target and structure to obtain a total dosage cost;

(c) accepting the proposed radiation beam arrangement of a given iteration if the total dosage cost of a given iteration is less than the total dosage cost of the previous iteration;

(d) rejecting the proposed radiation beam arrangement of a given iteration if the total dosage cost of a given iteration is greater than the total dosage cost of the previous iteration; and (e) repeating steps b–d until the proposed radiation beam arrangement has a total dosage cost value within an acceptable level to obtain an optimized radiation beam arrangement.

15. The method of claim 14, wherein the proposed radiation beam arrangement is calculated using simulated annealing radiation therapy planning methods.

16. The method of claim 14, further comprising the step of:

(f) applying the optimized radiation beam arrangement to the patient using a conformal radiation therapy apparatus.

17. The method of claim 15, further comprising the step of:

(f) applying the optimized radiation beam arrangement to the patient using a conformal radiation therapy apparatus.

18. A method of determining an optimized radiation beam arrangement for applying radiation to a tumor target volume while minimizing radiation of a structure volume in a patient, comprising the steps of:

determining a desired CDVH for each of at least one target or structure, representing the desired cumulative effect of a radiation dose to be applied to the patient;

calculating a proposed radiation beam arrangement proposed to be applied to the patient, associated with a total dosage cost;

creating a proposed CDVH for each of the at least one target or structure, representing the cumulative effect of the proposed radiation beam arrangement;

assigning a plurality of cost zones for each of the desired CDVHs;

assigning a zone weight for each of the plurality of cost zones of each of the CDVHs;

determining a zone cost value representing a zone cost for each cost zone of each CDVH of each target and structure for each of the plurality of cost zones of each of the desired CDVHs by multiplying a value representing the cost zone's zone weight by a value representing the quotient of a value representing the cost zone's zone area bounded by the proposed CDVH and a value representing the cost zone's zone area bounded by the desired CDVH;

determining a total target cost value representing a cost of the proposed radiation beam arrangement for each of the at least one target by summing the zone cost values of each of the at least one target;

determining a total structure cost value representing a cost of the proposed radiation beam arrangement for each of the at least one structure by summing the zone cost values of each of the at least one structure; and determining a total dosage cost value representing the total cost of the proposed radiation beam arrangement by summing each target cost value and each structure cost value.

19. The method of claim 18, wherein the proposed radiation beam arrangement is calculated using simulated annealing radiation therapy planning methods.

20. The method of claim 18, further comprising the step of:

in response to the total dosage cost value, applying the proposed radiation beam arrangement to a patient by a conformal radiation therapy apparatus if the total dosage cost value is within an acceptable level or rejecting the proposed radiation beam arrangement if the total dosage cost value is outside an acceptable level.

21. The method of claim 19, further comprising the step of:

in response to the total dosage cost value, applying the proposed radiation beam arrangement to a patient by a conformal radiation therapy apparatus if the total dosage cost value is within an acceptable level or rejecting the radiation beam arrangement if the total dosage cost value is outside an acceptable level.

22. A method of determining an optimized radiation beam arrangement for applying radiation to a tumor target volume while minimizing radiation of a structure volume in a patient, comprising the steps of:

using a computer to computationally obtain a proposed radiation beam arrangement;

using a computer to computationally change the proposed radiation beam arrangement iteratively, incorporating a cost function at each iteration to approach correspondence of partial volume data associated with the proposed radiation beam arrangement to partial volume data associated with a pre-determined desired dose prescription, wherein the proposed radiation beam arrangement is changed by changing the beam weights; and rejecting the change of the proposed radiation beam arrangement if the change of the proposed radiation beam arrangement leads to a lesser correspondence to the desired prescription and accepting the change of the proposed radiation beam arrangement if the change of the proposed radiation beam arrangement leads to a greater correspondence to the desired prescription to obtain an optimized radiation beam arrangement.

23. The method of claim 22, wherein the partial volume data is entered directly into the computer.

24. The method of claim 22, wherein the partial volume data is calculated by the computer based on a CDVH graphically entered into the computer using a pointing device.

25. An apparatus for determining an optimized radiation beam arrangement for applying radiation to a tumor target volume while minimizing radiation of a structure volume in a patient, comprising:

a computer, adapted to computationally obtain a proposed radiation beam arrangement, the computer further adapted to computationally change the proposed radiation beam arrangement iteratively, wherein the proposed radiation beam arrangement is changed by changing the beam weights, the computer further adapted to incorporate a cost function at each iteration to approach correspondence of partial volume data associated with the proposed radiation beam arrangement to partial volume data associated with a pre-determined desired dose prescription, and the computer further adapted to reject the change of the proposed radiation beam arrangement if the change of the proposed radiation beam arrangement leads to a lesser correspondence to the desired dose prescription and to accept the change of the proposed radiation beam arrangement if the change of the proposed radiation beam arrangement leads to a greater correspondence to the desired dose prescription to obtain an optimized radiation beam arrangement.

26. The apparatus of claim 25, wherein the partial volume data is represented as a CDVH.

27. The apparatus of claim 25, further comprising:

a conformal radiation therapy apparatus in communication with the computer for applying the optimized radiation beam arrangement to the patient.

28. The apparatus of claim 27, wherein the partial volume data is represented as a CDVH.

29. An apparatus for determining an optimized radiation beam arrangement for applying radiation to a tumor target volume while minimizing radiation of a structure volume in a patient, comprising a computer, including:

means for computationally obtaining a proposed radiation beam arrangement;

means for computationally changing the proposed radiation beam arrangement iteratively, wherein the means for computationally changing the proposed radiation beam arrangement includes a means for changing the beam weights;

means for incorporating a cost function at each iteration to approach correspondence of partial volume data associated with the proposed radiation beam arrangement to partial volume data associated with a predetermined desired dose prescription; and means for rejecting the change of the proposed radiation beam arrangement if the change of the proposed radiation beam arrangement leads to a lesser correspondence to the desired dose prescription and accepting the change of the proposed radiation beam arrangement if the change of the proposed radiation beam arrangement leads to a greater correspondence to the desired dose prescription to obtain an optimized radiation beam arrangement.

30. The apparatus of claim 29, wherein the partial volume data is represented by a CDVH.

31. The apparatus of claim 29, further comprising a conformal radiation therapy apparatus in communication with the computer for applying the optimized radiation beam arrangement to the patient.

32. The apparatus of claim 31, wherein the partial volume data is represented by a CDVH.

33. A method of determining an optimized radiation beam arrangement for applying radiation to at least one tumor target volume while minimizing radiation to at least one structure volume in a patient, comprising the steps of:

distinguishing each of the at least one tumor target volume and each of the at least one structure volume by target or structure type, wherein the target or structure types are distinguished as either Biologically Uniform or Biologically Polymorphic;

determining desired partial volume data for each of the at least one target volume and structure volume associated with a desired dose prescription;

entering the desired partial volume data into a computer;

in response to the desired partial volume data and in response to the target or structure type of each of the at least one tumor target volume and each of the at least one structure volume, using the computer to computationally calculate an optimized radiation beam arrangement.

34. The method of claim 33, further comprising the step of applying the optimized radiation beam arrangement to the patient with a conformal radiation therapy apparatus.

35. The method of claim 33, wherein the optimized radiation beam arrangement is calculated using different cost function parameters depending on the target or structure type.

36. An apparatus for determining an optimized radiation beam arrangement for applying radiation to a tumor target volume while minimizing radiation of a structure volume in a patient, comprising:

a computer, adapted to computationally obtain a proposed radiation beam arrangement;

the computer further adapted to computationally change the proposed radiation beam arrangement iteratively, wherein the proposed radiation beam arrangement is changed by changing the beam weights, the computer further adapted to incorporate a cost function at each iteration to approach correspondence of partial volume data associated with the proposed radiation beam arrangement to partial volume data associated with a pre-determined desired dose prescription, and the computer further adapted to reject the change of the proposed radiation beam arrangement if the change of the proposed radiation beam arrangement leads to a lesser correspondence to the desired dose prescription and to accept the change of the proposed radiation beam arrangement if the change of the proposed radiation beam arrangement leads to a greater correspondence to the desired dose prescription to obtain an optimized radiation beam arrangement.

37. The apparatus of claim 36, wherein the partial volume data is represented by a CDVH.

38. The apparatus of claim 36, further comprising:

a conformal radiation therapy apparatus in communication with the computer for applying the optimized radiation beam arrangement to the patient.

39. The apparatus of claim 38, wherein the partial volume data is represented by a CDVH.

40. A method of determining an optimized radiation beam arrangement for applying radiation to at least one tumor target volume while minimizing radiation of at least one structure volume in a patient, comprising the steps of:

determining desired partial volume data for each of the at least one target volume and structure volume associated with a desired dose prescription;

entering the desired partial volume data into a computer;

in response to the desired partial volume data, using the computer to computationally approximate desired CDVHs for each of the at least one target and structure associated with the desired dose prescription; and using the computer to computationally calculate the optimized radiation beam arrangement associated with the CDVHs approximated by the computer.

41. The method of claim 40, wherein the desired CDVHs are computationally constructed by the computer based on numerical values representing the partial volume data entered into the computer.

42. The method of claim 40, further comprising the step of applying the optimized radiation beam arrangement to the patient with a conformal radiation therapy apparatus.

43. The method of claim 40, wherein the optimized radiation beam arrangement is calculated using simulated annealing radiation therapy planning methods.

44. The method of claim 40, wherein the CDVHs approximated by the computer are approximated by the steps of:

using the computer to computationally obtain a set of proposed beam weights;

using the computer to computationally change the set of proposed beam weights iteratively, incorporating a cost function at each iteration to determine a cost of the change to the set of proposed beam weights; and rejecting the change to the set of proposed beam weights if the change to the set of proposed beam weights leads to a lesser correspondence to the desired CDVHs and accepting the change to the set of proposed beam weights if the change to the set of proposed beam weights leads to a greater correspondence to the desired CDVHs.

45. The method of claim 44, wherein the optimized radiation beam arrangement is calculated using simulated annealing radiation therapy planning methods.

46. The method of claim 44, further comprising the step of applying the optimized radiation beam arrangement to the patient with a conformal radiation therapy apparatus.

47. The method of claim 44, wherein the desired CDVHs are computationally constructed by the computer based on numerical values representing the partial volume data entered into the computer.

* * * * *